US008152796B2

(12) United States Patent
McMillan

(10) Patent No.: US 8,152,796 B2
(45) Date of Patent: Apr. 10, 2012

(54) METHOD AND APPARATUS FOR PERFORMING PERCUTANEOUS LASER DISC DECOMPRESSION WITH VAPORIZATION MONITORING BY FLUID DISPLACEMENT

(76) Inventor: Marion R. McMillan, Seneca, SC (US)

( * ) Notice: Subject to any disclaimer, the term of this patent is extended or adjusted under 35 U.S.C. 154(b) by 1472 days.

(21) Appl. No.: 11/699,527

(22) Filed: Jan. 29, 2007

(65) Prior Publication Data

US 2008/0140023 A1  Jun. 12, 2008

(51) Int. Cl.
*A61B 18/20* (2006.01)

(52) U.S. Cl. .............................. 606/11; 128/898; 606/15

(58) Field of Classification Search ................. 606/2–19; 128/898
See application file for complete search history.

(56) References Cited

U.S. PATENT DOCUMENTS

| 5,084,043 A | 1/1992 | Hertzmann et al. ............... 606/3 |
| 5,320,617 A | 6/1994 | Leach ............................ 606/15 |
| 5,437,661 A | 8/1995 | Rieser ............................ 606/15 |
| 5,628,734 A | 5/1997 | Hatfalvi ......................... 604/272 |
| 5,871,470 A | 2/1999 | McWha .......................... 604/158 |
| 5,948,008 A * | 9/1999 | Daikuzono ...................... 607/89 |
| 6,767,347 B2 | 7/2004 | Sharkey et al. ................. 606/41 |
| 6,890,332 B2 * | 5/2005 | Truckai et al. .................. 606/41 |
| 2005/0256513 A1 | 11/2005 | Murray et al. ..................... 606/3 |

FOREIGN PATENT DOCUMENTS

JP  11-151247  8/1999

* cited by examiner

*Primary Examiner* — Henry M Johnson, III
(74) *Attorney, Agent, or Firm* — Sara C. Kanos; Nexsenpruet, LLC

(57) ABSTRACT

Apparatus and method of performing percutaneous laser spinal disc decompression with the patient retaining consciousness. The clear plastic hub of a discectomy needle has a translucent hub with a chamber which is filled with a saline solution prior to insertion of an optical fiber of a laser apparatus through the needle. Gas production from the vaporization of the nucleus of the disc by the optical fiber of the laser apparatus forms bubbles in the water or saline fluid interface thereby providing the physician with an indication of the rate of vaporization of the disc nucleus. In addition, the detection of gas bubbles in an awake, responsive patent facilitates (a) determining the appropriate amount of laser energy required, (b) confirmation of disc vaporization, (c) following the course of laser surgery, and (d) minimizing the potential for laser associated patient injury.

7 Claims, 5 Drawing Sheets

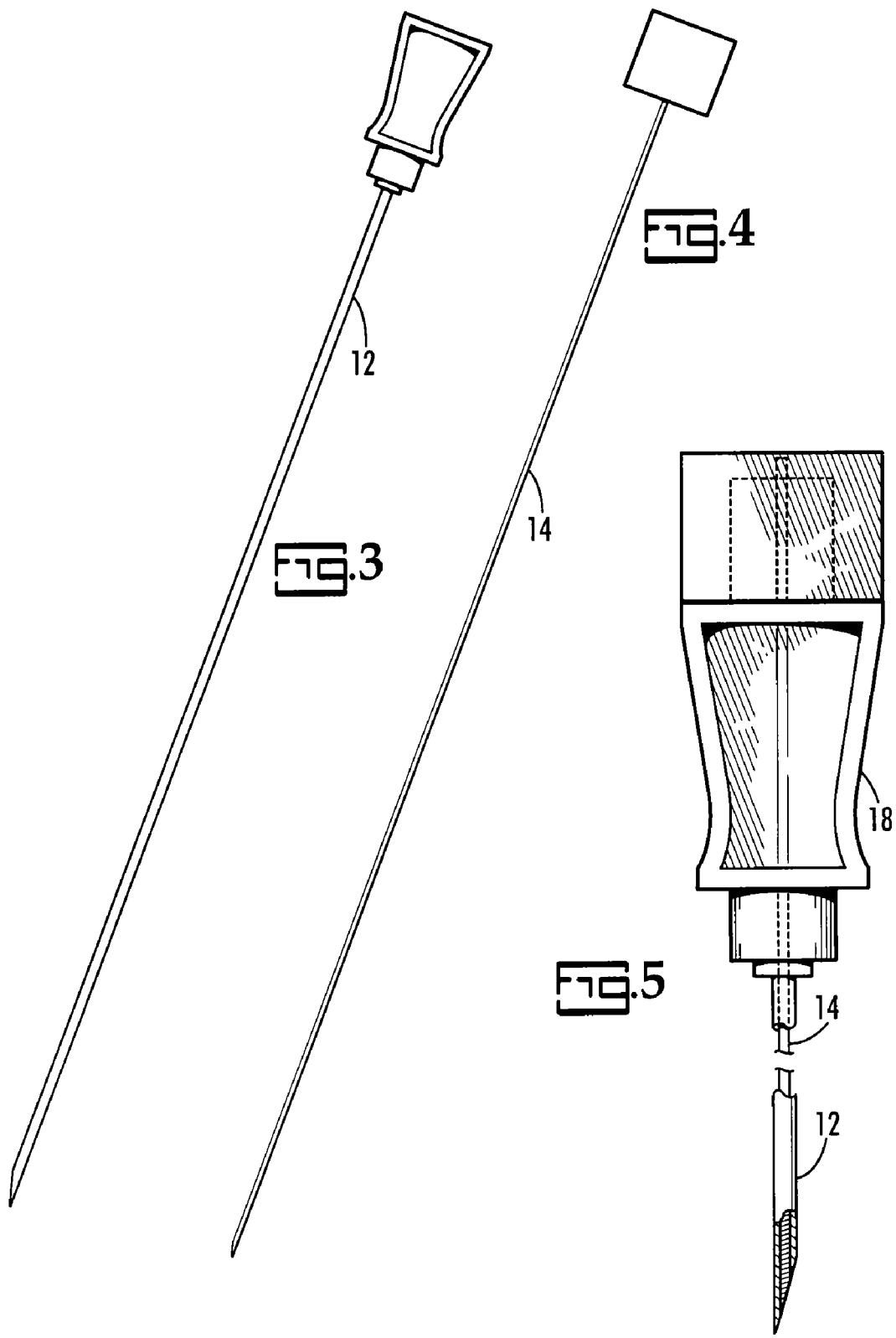

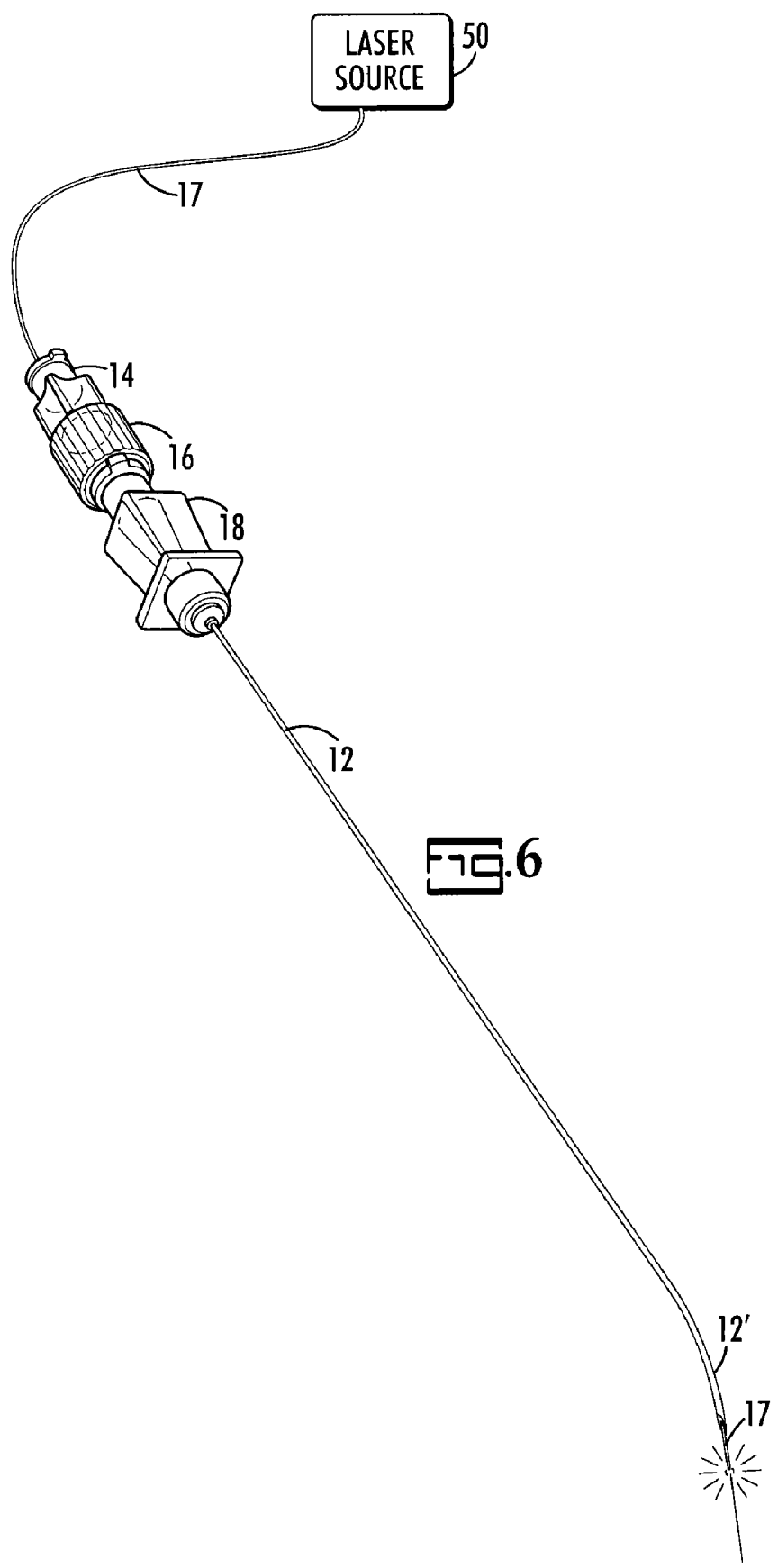

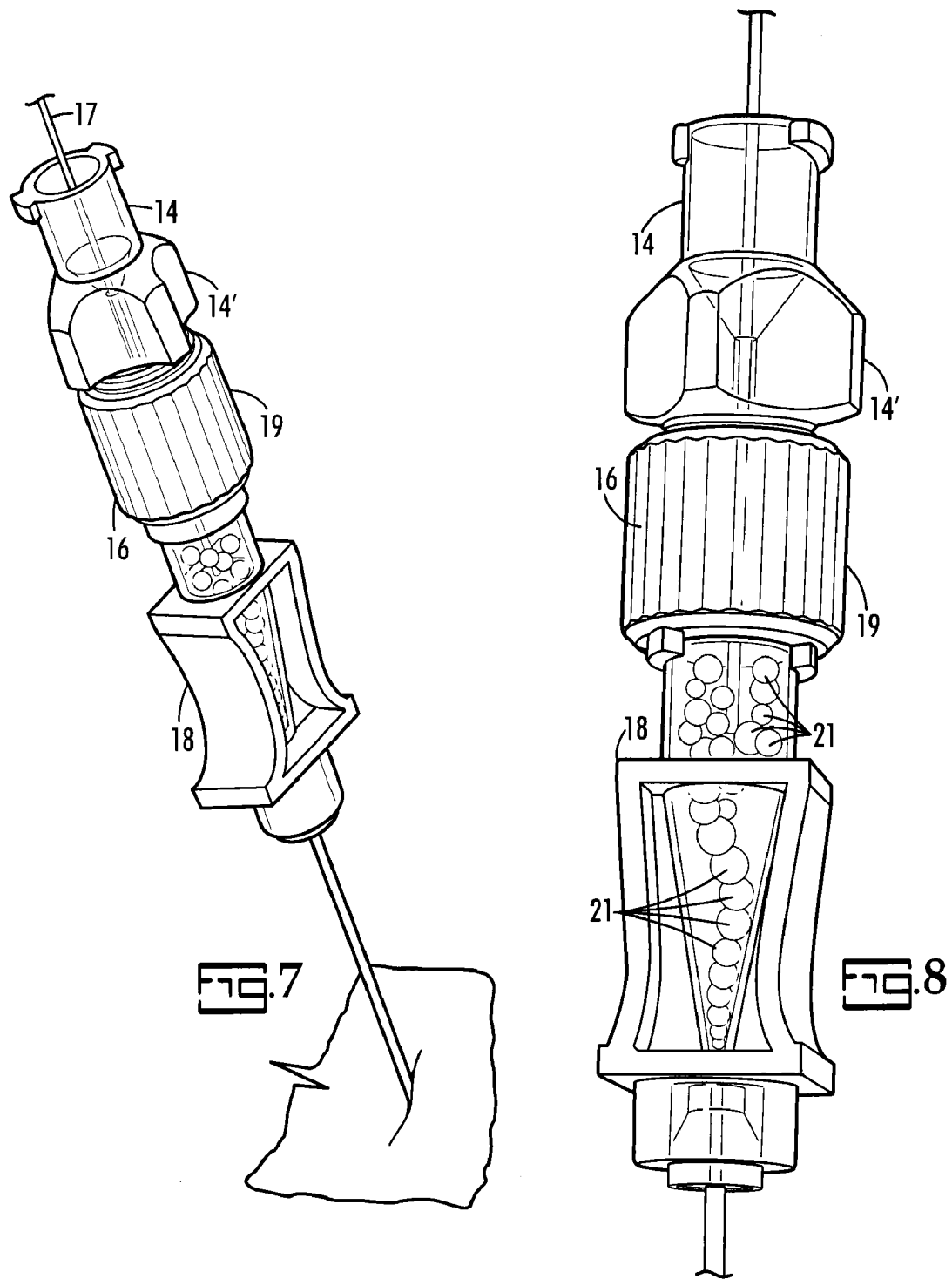

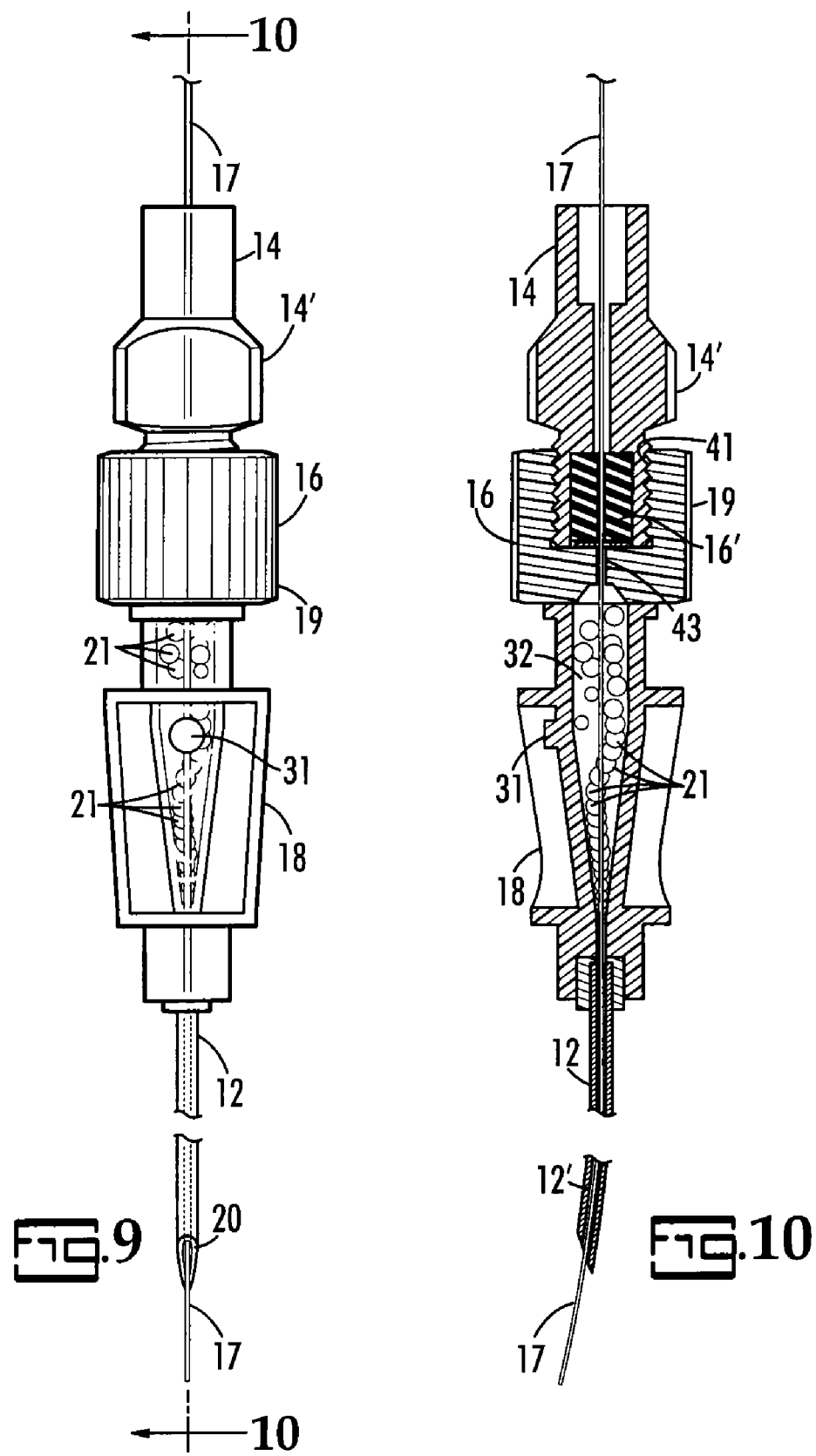

METHOD AND APPARATUS FOR PERFORMING PERCUTANEOUS LASER DISC DECOMPRESSION WITH VAPORIZATION MONITORING BY FLUID DISPLACEMENT

BACKGROUND OF THE INVENTION

Percutaneous laser disc decompression using the neodymium-YAG (Nd:YAG) laser operating at 1064 nanometers (nm) has been described by Choy and colleagues as a minimally invasive alternative to open surgical decompression for treatment of painful degenerated and herniated lumbar and cervical discs. The tissue absorption characteristics of the Nd:YAG laser at 1064 nm are considered optimal for this indication such that a controlled, reproducible vaporization defect may be produced to achieve the therapeutic effect with minimal risk of thermal injury. Accordingly, laser disc decompression may be safely performed without the need for tissue cooling or direct visual monitoring of the lasing procedure, or the added bulk, size, and expense of these added devices. The method has been determined to be safe and effective when used on an outpatient basis with local anesthesia and conscious sedation. U.S. Pat. No. 5,084,008 shows an attempt to refine the technique using large bore curved probes to introduce the optical delivery system and increase the efficiency of tissue removal by deflection of the laser beam around a circular arc. U.S. Pat. No. 5,948,008 discloses use of smaller probes with temperature and ultrasonic monitoring devices to increase patient comfort and reduce the likelihood of thermal injury to patients.

SUMMARY OF THE INVENTION

The present invention further refines the technique of laser discectomy and increases the comfort of the procedure by using a smaller 20 Birmingham gauge bore needle, curved at its distal end to facilitate needle placement. The proximal end of the needle is outfitted with a clear plastic hub having a chamber which is filled with a column of saline solution or water to allow monitoring of the progress and course of laser disc vaporization without the use of endoscopic or ultrasonic monitoring methods. It is desirable for the distal end of the needle to be bent slightly to facilitate desired placement of the needle tip within the disc nucleus. During the course of tissue vaporization, vapor or gas bubbles are produced. Observation of the production of gas bubbles passing through the fluid column during disc vaporization in a responsive, lightly sedated patient allows the attending physician to monitor the course of laser discectomy and accurately titrate the amount of laser energy delivered to the patient, thus minimizing the risk of thermal injury to the disc and contiguous tissues, and also maximizing patient comfort. Moreover, observing the production of gas bubbles provides accurate documentation of disc vaporization required to achieve the therapeutic effect of laser discectomy.

BRIEF DESCRIPTION OF THE DRAWINGS

The invention is illustrated in the accompanying drawings, in which:

FIG. 3 is a side view of a 20 gauge needle;

FIG. 4 is a side view of a stylette for the 20 gauge needle of FIG. 3;

FIG. 5 is a side view showing the stylette inserted into the 20 gauge needle with parts broken away for illustration purposes;

FIG. 6 shows the apparatus for performing the percutaneous laser disc decompressions;

FIG. 7 shows a needle inserted into a human disc with an optical fiber transmitting a laser beam;

FIG. 8 shows a transparent needle hub filled with water and vapor bubbles rising from the laser treated herniated disc;

FIG. 9 is a side view of the needle, the needle hub, the laser transmitting optical fiber and its compression nut unit, and FIG. 10 is a section taken on line 10-10 in FIG. 9.

DETAILED DESCRIPTION OF THE INVENTION

Figure 1:
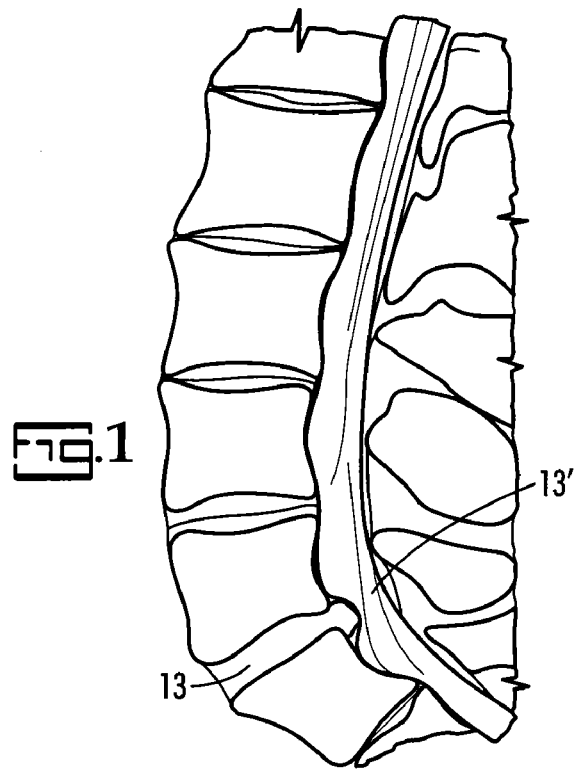
FIG. 1 is a side view of a spine showing a herniated lumbar disc.
Figure 2:
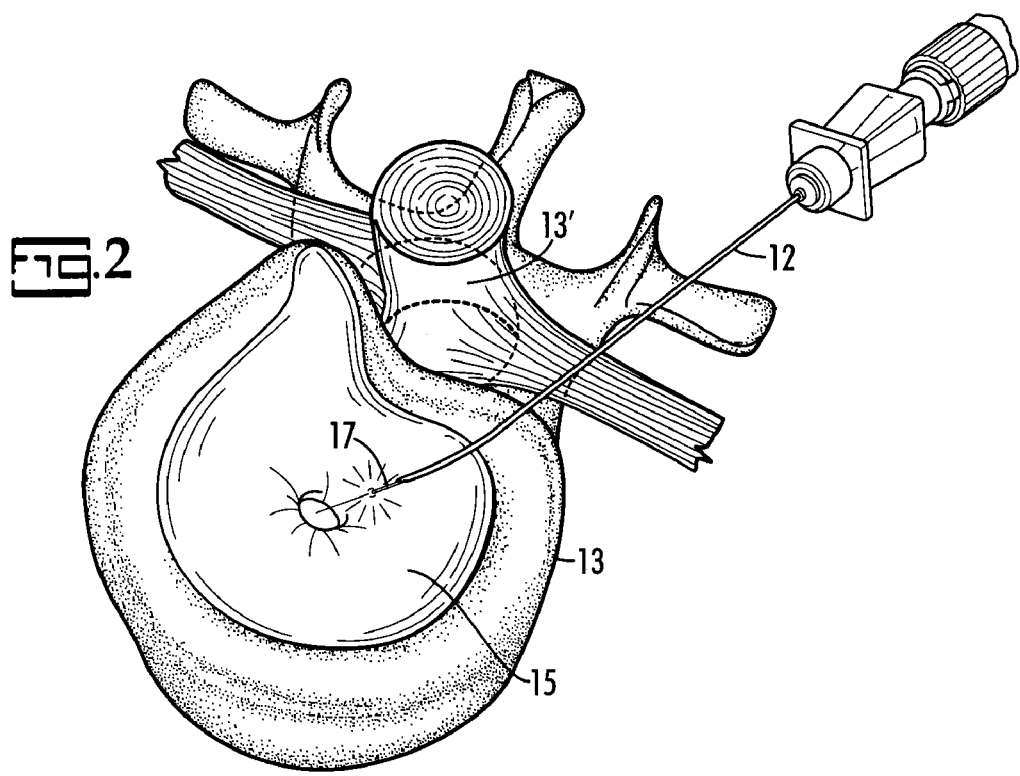
FIG. 2 shows laser discectomy of a herniated disc.

The patient is prepared for surgery by the placement of a peripheral venous cannula and administration of preoperative intravenous antibiotics. The patient is brought into the operating room where sterile preparation and drapes are applied and local anesthesia with conscious sedation is administered. It is important that patients be able to provide continuous verbal communication to detect and prevent thermal or nerve injury during the procedure.

After fluoroscopic localization of the disc to be treated through use of at least two fluoroscopic images, local anesthesia is administered to the skin entry site. The 20 gauge discectomy needle 12 shown in FIG. 3, with the stylette 14 shown in FIG. 4 inserted therein, is placed over the x-ray projection of the subject disc from a right or left sided approach corresponding to the predominant side of radicular symptoms. In the preferred embodiment of the invention, the needle 12 is provided with a clear plastic hub 18 and a one centimeter long 10 degree curved tip 12' which greatly facilitates the steering and guidance of the needle 12 into the nucleus pulpous 15 the disc 13 in an orientation considered optimal by the treating physician and confirmed in two fluoroscopic views. The needle 12 and the stylette 14 have coplanar tapered tips. It is essential that the needle 12 be placed in a plane parallel to the long axis of the disc 13 within the disc nucleus pulpous 15, and bisecting the disc 13 to minimize the risk of thermal injury to the disc endplates and contiguous structures. A marker 31 is provided on the radial side of the hub 18 corresponding to the radial direction of the bend in distal end 12' of the needle 12. The marker 31 provides the surgeon with a direct visual indication of the orientation of the curved end of the needle 12. After the desired placement of the needle 12 has been achieved, the stylette 14 is withdrawn from the needle. The clear plastic hub 18 of the needle 12 is next filed with a transparent fluid column such as water or a saline solution.

A 1064 nm optical wave length variable intensity and variable duration laser delivery system 14, as shown in FIGS. 6 through 10, includes a screw 14' which is threaded into an internally threaded opening 41 at one end of a locking nut 19 of a compression depth limiting device 16, as shown in FIG. 10. The nut 19 has an unthreaded part, axially adjacent to its threaded part, which has a cylindrical bore 43 whose diameter is smaller than the adjacent threaded opening 41, but is slightly larger than the diameter of the fiber 17. The pressure exerted by the threaded end of the screw 14' compresses a deformable rubber cylinder 16' which in turn applies radial inward pressure against the fiber 17 to prevent linear movement thereof. The laser delivery system 14 is calibrated in an appropriate manner to determine its optical transmission characteristics prior to the start of the laser procedure.

The laser source 50 is initially programmed to deliver pulses of laser energy through the optical fiber 17 at initial amplitude of 20 watts per pulse of 0.5 to 2.0 seconds duration. The optical fiber 17 extending from the nut 19 of the compression depth limiting device 16 is next calibrated for optical transmission and placed into the interior of the needle 12 by way of its transparent hub 18 so that the tip of the optical fiber 17 protrudes 1 to 5 mm from the beveled needle opening 20, depending on the placement and orientation of the needle 12 in the disc 13 and the preference of the surgeon. Lasing can then begin. In the preferred process the individual pulses of laser light energy of amplitude 20 watts/pulse with pulse duration from 0.5 to 2.0 seconds/pulse are delivered at 1 to 3 second intervals. Alternatively, a continuous wave laser delivery method may be used if desired. The optical fiber 17 used to deliver the laser beam is comprised of a 0.40 millimeter diameter quartz rod with a plastic coating bringing it to a 0.50 millimeter outside diameter. The fiber 17 has an exterior diameter which is smaller than the interior diameter of the 20 gauge needle 12, whereby a passageway is provided for exit of vapors produced by the laser treatment. The 20 gauge needle has an outside diameter of 0.90 millimeter and an inside diameter of 0.64 millimeter.

In the preferred embodiment of the invention, the course and progress of tissue vaporization is monitored continuously by the direct production of gas bubbles 21 emanating past the 1064 nm optical wave length delivery system and into the fluid-filled hollow interior chamber 32 of the transparent plastic hub 18 of the needle 12. The vapor in the bubbles escapes to the atmosphere by way of the loose joint formed by the abutting ends of the nut 19 and the hub 18. Unlike direct visualization methods of monitoring the course and progress of tissue vaporization by the laser, such as endoscopy or ultrasonic visualization, monitoring of fluid displacement by observing gas bubbles 21 allows the use of the smallest possible surgical instrumentation yet proposed for percutaneous laser discectomy to provide maximum patient comfort and safety. The continuous monitoring of gas bubble production allows confirmation of tissue vaporization at the lowest possible or highest required levels of delivered laser energy needed to achieve the therapeutic effect. For example, if the initial laser power settings fail to produce disc vaporization by detection of gas bubbles, output power is incrementally increased until bubbles are formed or the awake responsive patient complains of procedural pain. Alternatively, if disc vaporization is confirmed by the production of gas bubbles at the initial power settings, laser output power may be reduced to the lowest setting at which gas bubbles are produced. In combination with the use of conscious sedation and an awake responsive patient, the risk of laser associated thermal injury is minimized and disc vaporization is assured without the need for bulky additional temperature measurement, ultrasonic, or direct endoscopic visualization methods, and the larger instrumentation they require.

In the preferred method of this invention, laser disc vaporization continues for 30 to 70 vaporizing pulses or until 600 to 1600 watts of total joules of laser energy is delivered to the disc 13, by pulsed or continuous technique. In the course of lasing, the distal tip of the optical delivery system may become frosted and birefringent as a result of the absorption of laser heat, and thereby lose its optical transmission ability. The tip must be visually inspected every 200 to 300 joules of delivered energy to verify its integrity and to allow tip reconditioning as needed. Multiple intradiscal lesions may be given if desired, keeping the plane of the vaporization channel within the plane bisecting the disc thickness as described initially. Beam deflection through a radial arc, as disclosed in U.S. Pat. No. 5,084,008, is neither useful or desired, and may increase the risk of thermal injury to the disc endplate. At the completion of the procedure, intradiscal analgesics and antibiotics are routinely administered, but corticosteroid preparations are avoided. Multiple discs may be treated as described, if indicated. At the completion of surgery a sterile strip dressing is applied and the patient allowed to ambulate home.

What is claimed is:

1. Apparatus for performing lumbar and cervical disc nucleus vaporization using laser energy, comprising:
    a needle assembly including
        an elongated hollow needle of predetermined interior diameter having an open proximal end and an open distal end and a translucent needle hub to which said proximal end of said needle is rigidly secured including a chamber in fluid communication with said open proximal end of said needle and having an opening adapted for communication with the atmosphere,
    a needle stylette removable from said needle,
    a variable intensity and variable duration laser delivery system including an optical fiber having a exterior diameter smaller than the interior diameter of said hollow needle so as to be insertable through the interior of said hollow needle, and so as to allow for vapor passage, and an adjustable optical fiber depth limiting device operable to select the length of optical fiber extending from said distal end of said needle and a saline solution in said chamber of said needle hub through which bubbles of vapor created by laser vaporization of said nucleus pass and are visibly observable by an attendant physician.

2. The apparatus of claim 1 wherein said needle is not larger than a 20 gauge needle.

3. The apparatus of claim 1 wherein said distal end of said needle is bent 10 degrees to provide a one centimeter long curved tip.

4. The apparatus of claim 3 including a visible marker on a radial side of said needle hub corresponding to the radial direction in which the distal end of said needle is bent.

5. The apparatus of claim 1 wherein said optical fiber is a 0.400 millimeter diameter quartz rod with a plastic coating having a 0.500 millimeter outside diameter.

6. A method of performing percutaneous laser spinal disc decompression comprising the steps of:
    providing a laser energy source,
    providing a styletted needle which has transparent hub with an open chamber at its proximal end,
    providing a variable intensity and variable duration laser delivery apparatus including a laser fiber with an adjustable compression nut, said laser fiber having a diameter smaller than the inside diameter of said styletted needle,
    providing an optical laser fiber,
    calibrating the optical laser fiber preoperatively to determine its optical transmission characteristics,
    with the stylette removed from the needle, placing the laser fiber in the needle and adjust the compression nut on the fiber so that the fiber extends between 1 mm and 5 mm from the distal end of the needle when the nut abuts the hub,
    using fluoroscopic guidance, placing the distal end of the styletted needle into the nucleus of a herniated or degenerated spinal disc of a patient under local anesthesia with conscious patent sedation permitting continuous verbal communication,
    removing stylette from the needle,
    placing a transparent fluid in the cavity of the hub of the needle,
    inserting the optical fiber of the laser delivery apparatus through the proximal end of the needle, adjusting the compression nut so that the optical fiber extends from 1 mm to 5 mm from the distal end of the needle when the nut rests on the hub of the needle, operating the laser apparatus to apply sufficient laser energy to the nucleus of the spinal disc to cause tissue vaporization, regulating the intensity and duration of the application of laser energy by observing bubble formation in the fluid filled chamber of the transparent needle hub and by verbal communication with the conscious patient.

7. A method of performing percutaneous laser spinal disc decompression, comprising the steps of providing a laser energy source, providing a variable intensity laser delivery apparatus including an optical fiber with a locking nut, providing a styletted needle having a tip at its distal end and a transparent hub with an open chamber at its proximal end, adjusting the locking nut so that the optical fiber projects between 1 mm and 5 mm from the distal end of the needle when the optical fiber is inserted herein with the locking nut abutting the transparent hub, preparing a human patient for a surgical procedure during which the patient retains consciousness, locating the disc to be treated using at least two fluoroscopic images, calibrating the optical laser fiber to verify its optical transmission characteristics prior to the start of the laser procedure, inserting the distal end of the styletted needle into the located disc with the distal end lying in the disc nucleus in a plane parallel to the long axis of the disc, removing the stylette, filling the hollow chamber of the transparent hub with a sterile water or saline liquid solution inserting the optical fiber through the needle projecting the end of said fiber 1 mm to 5 mm beyond the opening in the tip of the needle, delivering laser energy through the optical fiber to the disc nucleus, monitor the rate of vaporization of the nucleus by visibly observing vapor bubbles passing through the saline solution in the hollow chamber of the hub, and adjusting the laser energy delivery responsive to the observed rate of passage of the vapor bubbles passing through the saline solution and in response to patients verbal communication of experienced pain, delivering 30 to 70 vaporizing pulses producing 600 to 1600 total joules of laser energy to the disc nucleus by pulsed technique.

* * * * *